US00PP24583P3

(12) United States Plant Patent
Cain

(10) Patent No.: US PP24,583 P3
(45) Date of Patent: Jul. 1, 2014

(54) GRAPEVINE PLANT NAMED 'IFG TEN'

(50) Latin Name: *Vitis vinifera*
Varietal Denomination: IFG Ten

(75) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 206 days.

(21) Appl. No.: 13/507,266

(22) Filed: Jun. 18, 2012

(65) Prior Publication Data

US 2013/0340133 P1 Dec. 19, 2013

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Wendy C Haas

(57) ABSTRACT

A new and distinct grapevine variety denominated 'IFG Ten' is characterized by producing large, very crisp, oval, green, seedless berries borne on medium size clusters. The fruit ripen and are commercially harvestable in mid-season.

1 Drawing Sheet

Latin name of the genus and species claimed: *Vitis vinifera*. Variety denomination: 'IFG Ten'.

BACKGROUND OF THE INVENTION

The new and distinct grapevine described and claimed herein originated from a hand pollination of the USDA selection B31-164 and the Princess variety (USDA variety non-patented) performed in May 2003. The resulting plants were planted into the field in April 2004. The present variety of grapevine was selected as a single plant in August 2005 and was first asexually propagated by hardwood cuttings in December 2005. The resulting propagules were planted during April 2006 near Delano, Kern County Calif. and were found to reproduce true-to-type through at least two generations of asexual propagation.

BRIEF SUMMARY OF THE INVENTION

The new grapevine 'IFG Ten' is characterized by producing naturally large, oval, seedless berries having an occasional noticeable seed trace. Berries are very firm and crisp in texture and ripen in mid-season. Fruits normally ripen in mid August, about with or just slightly later than the Thompson Seedless variety near Delano, Calif.

To the inventor's knowledge, the known variety which the new grapevine variety is most similar to is its parent the Princess variety. 'IFG Ten' can be distinguished from the Princess variety by having a more oval shape as opposed to the more blocky, cylindrical shape of the Princess variety. The flesh of the 'IFG Ten' is more crisp than the flesh of the Princess variety and it is less prone to bruising and browning. The 'IFG Ten' has superior storage ability compared with the Princess variety. The 'IFG Ten' exhibits much less excessive flower abortion at bloom as compared with the Princess variety.

The 'IFG Ten' differs from the USDA B31-164 by producing yellow-green colored fruits as opposed to the red fruits of the USDA B31-164 variety.

BRIEF DESCRIPTION OF THE FIGURE

The accompanying photographic illustration in FIG. 1 illustrates in full color 'IFG Ten'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Ten' plants grown in the vicinity of Delano, Kern County, Calif. during 2009, and 2010 and is believed to apply to plants of the variety grown under similar conditions of soil and climate elsewhere

VINE

General:

*Size*.—Large.
*Vigor*.—Vigorous.
*Density of foliage*.—Dense.
*Productivity*.—Very productive.
*Root stock*.—Own root.
*Training method*.—Typically spur pruned leaving 2 bud spurs.

Trunk:
*Trunk diameter of* 4-*year-old vines at* 30 *cm above the soil line.*—5.5 cm.
*Shape.*—Medium.
*Straps.*—Short.
*Surface texture.*—Medium.
*Inner bark color.*—Greyed Orange;177A,177B.

SHOOTS

Young shoot:
*Form of tip.*—Fully opened.
*Distribution of anthocyanin coloration of tip.*—Absent — Very weak.
*Intensity of anthocyanin coloration of tip.*—Absent.
*Density of prostrate hairs of tip.*—Medium.
*Density of erect hairs of tip.*—Absent.
*Color.*—Yellow Green; 144A, N144A.
Woody shoot (Mature canes):
*Shape.*—Medium.
*Internode length.*—Medium; About 10.2 cm.
*Width at node.*—About 1.2 cm.
*Cross section.*—Circular.
*Surface.*—Striate.
*Main color.*—Greyed orange; N170B, 166C, 166D.
*Density of erect hairs of nodes.*—None.
*Density of erect hairs on internodes.*—None.
*Growth of axillary shoots.*—Weak. Approximately 8.7 cm.
Flowering shoot:
*Vigor during flowering.*—Medium.
*Attitude during flowering on shoots not tied.*—Semi-erect.
*Color.*—Dorsal side of internodes — Green with Red stripes.
*Color.*—Ventral side of internodes — Green.
*Color.*—Dorsal side of nodes — Green with Red stripes.
*Color.*—Ventral side of nodes — Green.
*Density of prostrate hairs of nodes.*—Very sparse.
*Density of erect hairs of nodes.*—None.
*Density of prostrate hairs on internode.*—None.
*Density of erect hairs on internode.*—None.
*Anthocyanin coloration of buds.*—Absent.
Tendrils:
*Distribution on the shoot* (*at full flowering*).—Discontinuous.
*Length of tendril.*—Medium-Long; About 21.1 cm.
*Thickness.*—Medium.
*Color.*—Yellow green; N144, 152B.
*Form.*—Bifurcated-Trifurcated.
*Number of consecutive tendrils.*—2.

LEAVES

Young leaves:
*Color of upper surface of first four distal unfolded leaves.*—Reddish.
*Average intensity of anthocyanin coloration of six distal leaves prior to flowering.*—Medium.
*Density of prostrate hairs between veins* (*lower surface*).—Very sparse.
*Density of prostrate hairs on veins* (*lower surface*).—Sparse.
*Density of erect hairs between veins* (*lower surface*).—Very sparse.
*Density of erect hairs on veins* (*lower surface*).—Sparse.
Mature leaves:
*Average length.*—About 15.3 cm.
*Average width.*—About 11.1 cm.
*Mature leaf size.*—Large.
*Shape of blade.*—Wedge-shaped.
*Number of lobes.*—5.
*Anthocyanin coloration of main veins on upper side of blade.*—Absent.
*Mature leaf profile.*—Involute.
*Blistering surface of blade upper surface.*—Very weak.
*Leaf blade tip.*—In the plane of the leaf.
*Undulation of margin.*—Slight.
*Thickness.*—Medium.
*Undulation of blade between main and lateral veins.*—Absent.
*Shape of teeth.*—Mixture of both sides straight and both sides convex.
*Length of teeth.*—Medium.
*Ratio length/width of teeth.*—Equal.
*Shape of upper lateral sinuses.*—Closed — Lobes slightly overlapping.
*Depth of upper lateral sinuses.*—Mixture of both Shallow and Medium.
*General shape petiole sinus.*—Closed — Lobes slightly overlapping.
*Shape of base of upper leaf sinuses.*—U-shaped.
*Tooth at petiole sinus.*—Absent.
*Density of prostrate hairs between veins on lower surface of blade.*—Very sparse.
*Density if erect hairs between veins on lower surface of blade.*—Very sparse.
*Density of prostrate hairs on main veins on lower surface of blade.*—None or very sparse.
*Density of erect hairs on main veins on lower surface of blade.*—Sparse.
*Density of prostrate hairs on main veins on upper surface of blade.*—Sparse.
*Density of erect hairs on main veins on upper surface of blade.*—None or very sparse.
*Autumn coloration of leaves.*—Greyed orange 163C, 161A, B, Greyed purple 18A, B, Greyed red 181A, B.
Upper surface:
*Color.*—Green; 137A, B.
*Anthocyanin coloration of main veins.*—Absent.
*Surface appearance.*—Glossy-Semi-glossy.
*Blistering surface of blade.*—Very weak.
Lower surface:
*Color.*—Yellow-Green; 144A, 146A, 146B.
*Anthocyanin coloration of main veins* (*lower surface*).—Absent.
*Glossiness.*—Medium.
*Surface texture.*—Smooth.
*Surface appearance.*—Semi-glossy.
Petiole:
*Length.*—About 10.2 cm.
*Length of petiole compared to middle vein.*—Slightly shorter.
*Density of prostrate hairs on petiole.*—Sparse.
*Density of erect hairs on petiole.*—None.
Buds:
*Bud fruitfulness.*—Basal: Mostly fruitful.
*Position of first fruitful shoot on previous season cane.*—$1^{st}$ to $2^{nd}$ node.
*Time of bud burst.*—Medium; Mar. 8, 2010.

FLOWERS

General:

*Flower sex*.—Hermaphrodite.

*Length of first inflorescence*.—Long; About 17.4 cm long by 11.8 cm wide.

*Position of first flowering and fruiting node*.—$2^{nd}$-$3^{rd}$.

*Number of inflorescence per flowering shoot*.—Usually 2.

*Time of bloom*.—Medium-late as compared with similar varieties in the growing area of Delano, Calif.

*Date of full bloom*.—Mar. 15, 2009.

FRUIT

General:

*Ripening period*.—Medium; Approximately Aug. 8, 2010.

*Use*.—Fresh market.

*Keeping quality*.—Excellent.

*Resistance to*.—Insects: Average typical of *Vitis vinifera* species. Diseases: Average typical of *Vitis vinifera* species.

*Shipping quality*.—Excellent.

*Refractometer test*.—Solid-sugar: About 17.2 Brix.

*Brix/acid*.—About 44.4.

*Titratable acidity*.—About 0.38.

*Juice pH*.—About 3.88.

Cluster:

*Mature cluster length* (*peduncle excluded*).—About 21.6 cm.

*Mature cluster width*.—About 16.8 cm.

*Mature cluster weight*.—About 903 gm.

*Bunch density*.—Medium.

*Number of berries*.—About 112.

*Form*.—Conical.

Peduncle:

*Lignification of peduncle*.—Weak.

*Length of peduncle*.—Approximately 3.6 cm.

Berry:

*Uniformity of size*.—Uniform.

*Single berry weight*.—About 7.9 gm natural; to about 8.4 gm when treated with gibberellic acid.

*Shape*.—Obtuse ovate.

*Seeds*.—Seed traces occasionally noticeable.

*Cross section*.—Circular.

*Berry dimensions*.—Longitudinal axis; About 2.6 cm, horizontal axis; About 2.2 cm.

*Berry firmness*.—Firm.

*Particular flavor*.—Neutral.

*Bloom* (*cuticular wax*).—Medium.

*Berry separation from pedicel*.—Medium.

*Skin color* (*without bloom*).—Yellow green; 145B.

Skin:

*Thickness*.—Thin.

*Texture*.—Tender.

*Reticulation*.—Absent.

*Tenacity*.—Tenacious to flesh.

What is claimed:

1. A new and distinct variety of grapevine as herein illustrated and described.

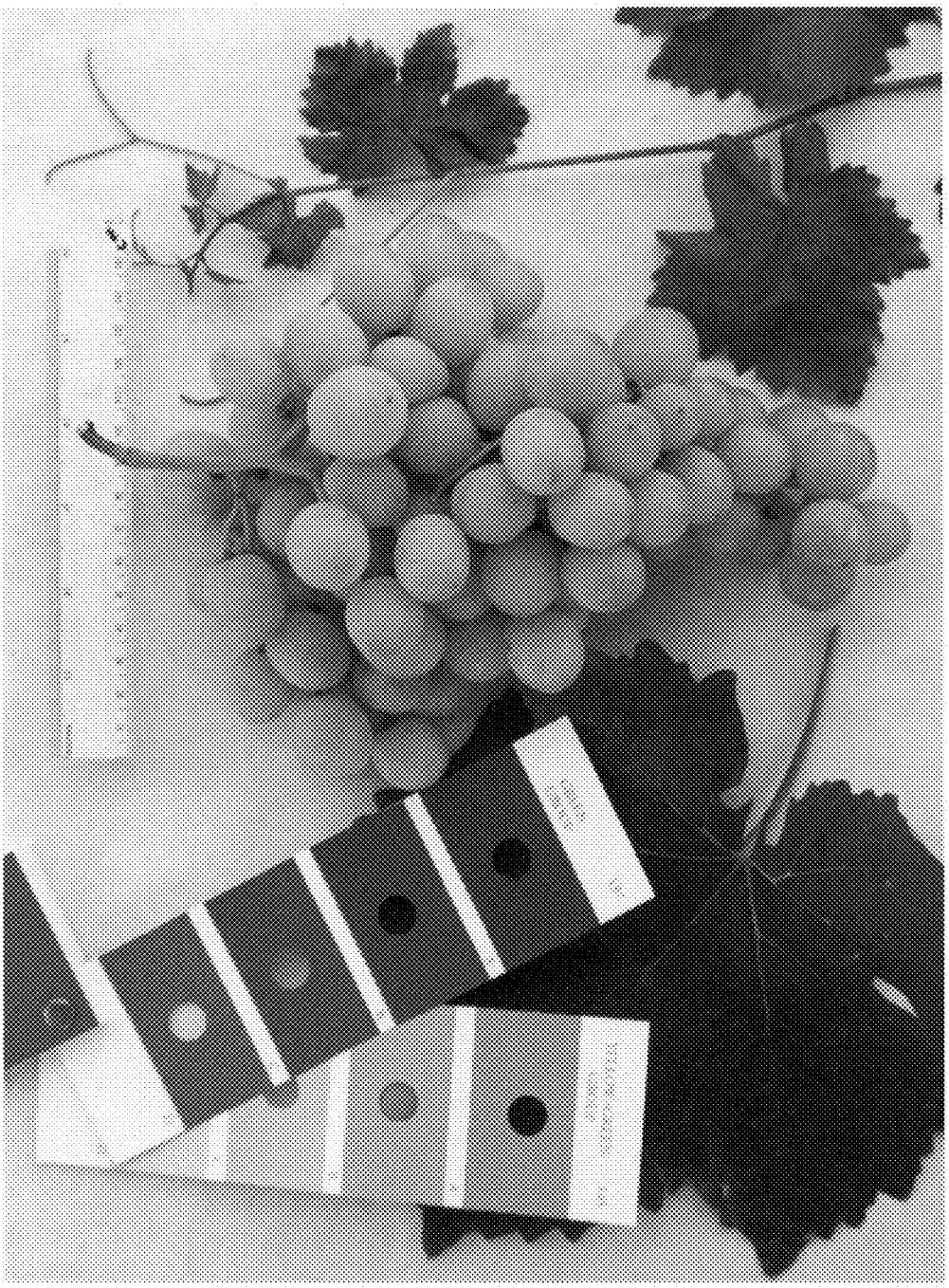

* * * * *